United States Patent [19]

Peck

[11] Patent Number: 4,494,001
[45] Date of Patent: Jan. 15, 1985

[54] DETECTION OF CONCEALED MATERIALS
[75] Inventor: Peter F. Peck, Wantage, England
[73] Assignee: United Kingdom Atomic Energy Authority, London, England
[21] Appl. No.: 168,359
[22] Filed: Jul. 15, 1980
[30] Foreign Application Priority Data Jul. 30, 1979 [GB] United Kingdom ............... 7926435

[51] Int. Cl.³ ............................................. G01N 23/00
[52] U.S. Cl. ................................. 250/358.1; 250/360.1
[58] Field of Search ............... 250/357, 358 R, 361 R, 250/363 R, 308

[56] References Cited

U.S. PATENT DOCUMENTS

| 3,068,359 | 12/1962 | Carlson | 250/361 R |
| 3,928,765 | 12/1975 | Teller | 250/358 R |
| 4,243,884 | 1/1981 | Avera, Jr. | 250/361 R |

FOREIGN PATENT DOCUMENTS

| 796788 | 6/1958 | United Kingdom . |
| 984454 | 2/1965 | United Kingdom . |
| 1045874 | 10/1966 | United Kingdom . |
| 1134806 | 11/1968 | United Kingdom . |
| 1530723 | 11/1978 | United Kingdom . |

Primary Examiner—Alfred E. Smith
Assistant Examiner—Janice A. Howell
Attorney, Agent, or Firm—Larson and Taylor

[57] ABSTRACT

A hand portable probe 11 contains a radioactive source capsule 16 of low energy γ rays which penetrate into an object against which the probe is positioned. Backscattered γ radiation is detected by an annular radiation detector array 14 positioned to be in contact with or very close to the surface under examination. Materials of low atomic number exhibit low photoelectric absorption and can be detected even when concealed behind steel.

2 Claims, 7 Drawing Figures

DETECTION OF CONCEALED MATERIALS

The invention relates to the inspection and analysis of materials within an object, in particular for the detection of concealed materials.

In the inspection and analysis of materials it is known to use various techniques of irradiation with ionising radiation and detection of the effects of scattering or absorption on the radiation or the radiation products of nuclear reactions between the incident radiation and the material under examination.

For example, there is described in Adventures in Experimental Physics 1975 in an article by A. Turkevitch et al an alpha scattering analysis instrument used in the NASA Surveyor missions for the first chemical analysis of the lunar surface.

The present invention is concerned with a device for providing an indication of the nature of materials within an object, and especially of materials concealed behind an opaque surface. For this a source of penetrating radiation, that is X-rays $\gamma$ rays or neutrons, is proposed, together with a detector which is sensitive to backscattered radiation.

It is desired that the device should be portable and for this a radioisotope radiation source is convenient as it requires no power supply and may be contained in a small, rugged capsule. However, it is clear that for such a device a source of as low intensity as possible should be employed and the intensity must, of course, be within the legal limits.

These desirable features and requirements and restrictions present several problems. Thus, to penetrate into the object under investigation with the maximum radiation intensity, the source should be as close as possible to the surface of the object.

The radiation detector has to intercept the maximum possible radiation backscattered from within the object and the minimum possible radiation either direct from the source or backscattered from any intervening opaque surface behind which the object may be concealed. Some compromise has to be accepted in meeting these requirements, because the maximum backscattered radiation is encountered close to the source and to the surface of the object under inspection, where direct radiation is also at a maximum. It is an object of the present invention to provide a solution to these problems.

The invention provides a device for indicating the nature of materials within an object, which device comprises a housing having a side wall adapted to be placed against an object to be inspected, a radioisotope source of penetrating radiation mounted within the housing close to but spaced from the said side wall, a scintillation or solid state radiation detector located closer to the said side wall than to the source of a collimator between the source and the detector to shield the detector from direct radiation from the source whilst permitting radiation from the source out of the housing transversely of the said side wall, detection and analysis of materials within the object being effected by measurement of radiation backscattered therefrom and detected in the radiation detector.

Preferably the radiation detector surface is as close as practicable to the inside surface of the said side wall.

Preferably a radiation detector array is located adjacent the said side wall in an annular configuration surrounding the radioisotope source.

Preferably the housing is constructed in the form of a hand portable probe.

A specific construction of device embodying the invention will now be described by way of example and with reference to the drawings filed herewith, in which.

Figure 1:
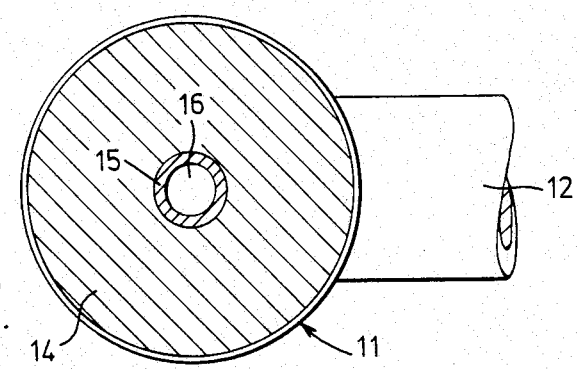
FIG. 1 is a diagrammatic sectional view of part of the device on the line 1—1 of FIG. 2.
Figure 2:
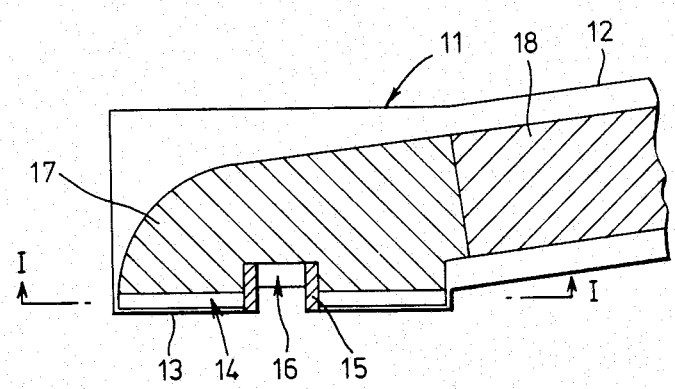
FIG. 2 is a diagrammatic side sectional view of part of the device.

Referring to FIGS. 1 and 2, the device comprises a cylindrical end housing 11 with a cylindrical side arm 12 attached thereto. The side arm, only part of which is shown in the drawings, provides a convenient handle for holding the device. Close to a side wall 13 of the housing 11 is an annular scintillation crystal 14. Within the central circular aperture of the scintillation crystal 14 is a short cylindrical collimator 15 in which, at the end remote from the side wall 13, is mounted a capsule 16 containing a radioactive material source which in this example is of $\gamma$ radiation. The capsule 16 has a tungsten alloy backing which shields radiation emanating from the source in the direction away from the side wall 13.

A light guide 17 provides an optical path for directing the light from scintillations in the crystal 14 onto a photomultiplier indicated diagrammatically at 18.

For detection and indication of backscattered radiation, any suitable conventional equipment may be used and is conveniently mounted in the side arm 12. However, the device of this example is particularly intended as a search device for detecting low atomic number materials, especially organic materials, concealed behind surfaces such as the metal skin of motor vehicles. For this, indication of a step change in backscattered intensity is particularly suitable and this is achieved by providing two rate meters to both of which is fed the backscatter count. The ratemeters have different rates of response to change in count rate. Under steady count rate conditions, their outputs will settle into balance and a detector subtracting one output from the other will give a zero indication. If the backscatter count rate changes, a difference between the ratemeter outputs appears, owing to their different rates of response to the change, this difference dying away with time. Differences thus detected are used, in this example, to change the pitch of an audible indicator tone.

The radioactive source and detector system are chosen according to the particular nature of investigation to be carried out by the device.

Thus, for search for low atomic number materials low energy $\gamma$ radiation is chosen. Although the scattering cross-section in this case is substantially independent of atomic number, the photoelectric absorption rises steeply with increasing atomic number. The net effect is therefore that more $\gamma$-radiation is backscattered from low atomic number material than from high atomic number material.

The energy of the γ-radiation is chosen to provide penetration of the thickness of the concealing surface expected to be met in the search. Thus $Co^{57}$ provides γ rays of energy 120 KeV which is adequate to penetrate steel up to ⅛ inch (3 mm) thick. $Cs^{137}$ provides γ rays of energy 662 KeV which is adequate to penetrate steel up to ¼ inch (6 mm) thick. $Co^{60}$ provides γ rays at energies of 1.17 MeV and 1.33 MeV which can penetrate steel up to ½ inch (12 mm) thick. It will be appreciated that the higher the γ radiation energy the greater will have to be the weight of collimator.

At low energies γ radiation is backscattered with very nearly the same energy as the incident radiation. It is therefore important that the detector is screened from receiving radiation direct from the source and that a minimum of radiation backscattered from the surface against which the device is placed should reach the detector.

The configuration of the device of this example meets these requirements particularly well. The arrangement enables the detector surface to be positioned as close as possible to actual contact with the surface under examination. This, together with the collimator configuration and recessed source, is effective to minimise incidence on the detector of direct radiation from the source and radiation scattered from the surface. An important characteristic in this respect is that, whilst both source and detector are ideally positioned as close as possible to the surface under examination, for practical reasons the detector has to be closer to the surface than the source. The annular configuration of the detector, with centrally located source, provides efficient interception of backscattered radiation such that, in the example using $Co^{57}$ source, a 3 millicurie source provides adequate intensity for a typical backscatter count rate of 10,000 counts per second. In this example a 1% change in count rate is the limit of sensitivity, this corresponding, by way of example, to the change in count rate produced by a package of about 25 grams of Heroin concealed behind ⅛ inch (3 mm) thick steel.

Figure 3:
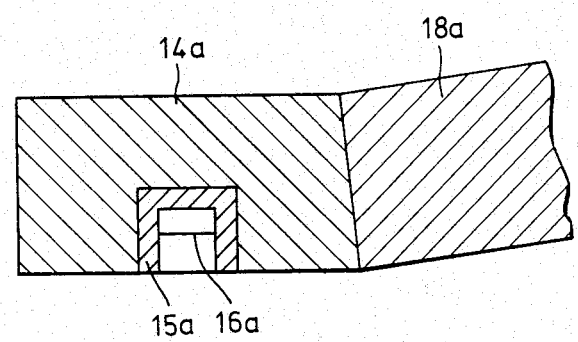
FIG. 3 is a diagrammatic side sectional view of another device.

FIG. 3 shows a modification of the device in which the source capsule 16a and collimator 15a are embedded in a cylindrical block of plastic or crystal scintillator 14a. This arrangement avoids the need for a separate light guide. The photomultiplier 18a mounted in a side arm may be positioned in any convenient orientation with respect to the scintillator 14a. It will be noted that the collimator 15a extends across the back of the space for the source capsule 16a so as to provide a firm base support for the capsule 16a.

Figure 4:
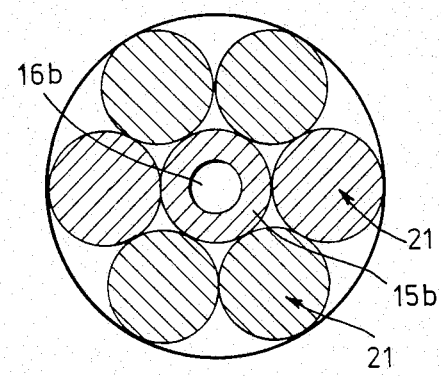
FIGS. 4 and 5 are respectively a diagrammatic sectional view on the line 4—4 of FIG. 5, and a diagrammatic side sectional view of part of another device.
Figure 5:
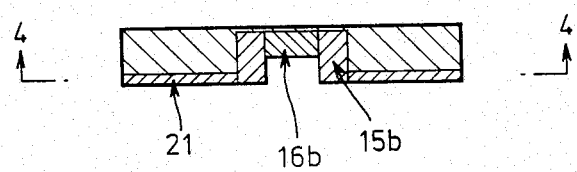

FIGS. 4 and 5 illustrate a further modified device, in which source capsule 16b and collimator 15b are surrounded by an annular array of circular semi-conductor detectors 21.

Figure 6:
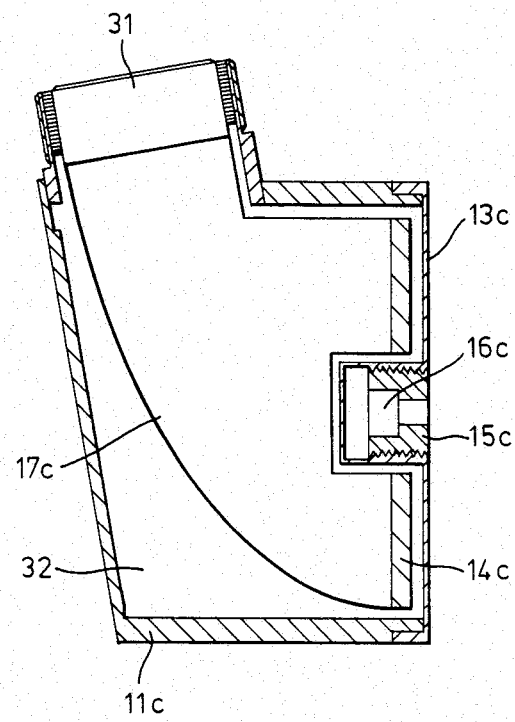
FIG. 6 is a side sectional view similar to FIG. 2 of a development of the device shown in FIG. 2.

FIG. 6 shows a development of the device of FIG. 2. Similar components are referenced with the same reference numerals distinguished by suffix "c". The light guide 17c is of perspex and couples to a window 31 of a photomultiplier (not shown in FIG. 6). The space between aluminium housing 11c and the combined light guide 17c and annular Na I (T1) scintillation crystal 14c is filled with magnesium oxide powder 32 to reflect light from the scintillation crystal 14c back into the light guide 17c. A thin layer of magnesium oxide is included between the scintillation crystal 14c and the side wall 13c, the consequent disadvantage of a small displacement away from optimum closeness of the crystal 14c to the side wall 13c being well worthwhile when weighed against the benefit of reflection back into the light guide 17c of light emitted from the crystal 14c towards the side wall 13c.

In the example of FIG. 6 collimation at 14c is provided by tungsten alloy material.

Figure 7:
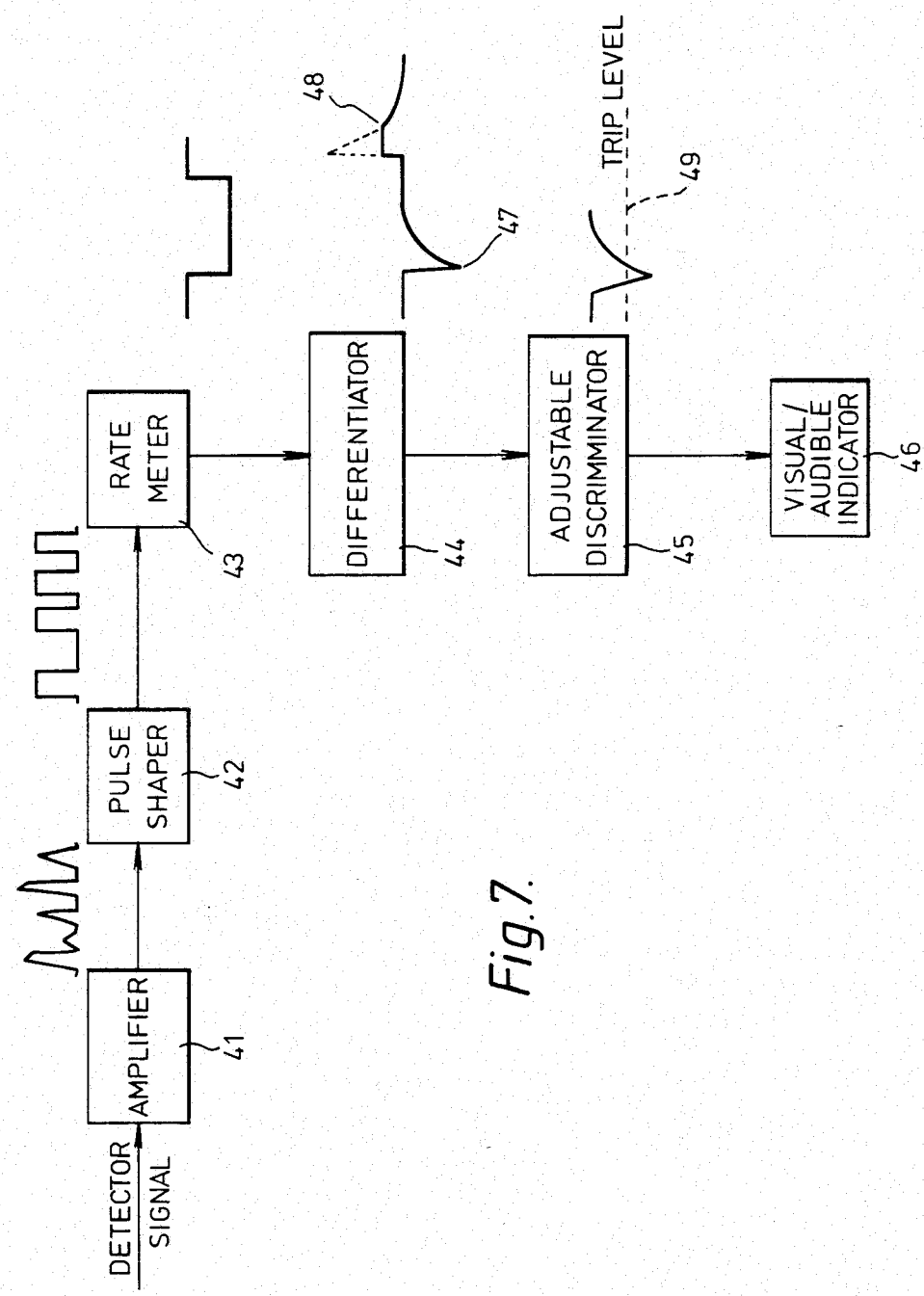
FIG. 7 is a block diagram of an electronic signal processing system to which any of the devices may be coupled.

FIG. 7 shows the electronic signal processing arrangement, which is a modification of that described above, for providing an audible and/or visual indication when the device detects the presence of low atomic number material concealed behind a thin layer of a relatively high atomic number material such as steel.

In FIG. 7 an indication of the electronic signal output waveform is shown adjacent each component.

The signal from the detector is amplified by amplifier 41 and fed to pulse shaper 42 and ratemeter 43 in a manner conventional in the art of processing electrical signals indicative of nuclear events. The output of ratemeter 43 is a signal level indicative of a rate of receipt of pulses from the pulse shaper 42. The signal level output from the ratemeter 43 only changes when the pulse rate changes.

Such changes in pulse rate are indicated by differentiator 44 which provides a negative-going spike, such as 47, whenever the ratemeter level increases.

A fall in ratemeter level will, of course, produce a positive going spike from the differentiator 44, but this is not used in the detection circuit and is cut-off as shown at 48 to reduce as far as practicable the recovery time of the differentiator 44.

Negative going spikes, such as 47, are tested by adjustable discriminator 45 against a trip level 49 and indicator 46 is triggered whenever the change in the pulse rate exceeds a predetermined amount. This predetermined amount is adjustable by changing the setting of the trip level 49 of the adjustable discriminator 45. It is particularly convenient for the indicator 46 to be an audible alarm, but visual indication as an alternative or in addition can readily be provided.

It will be appreciated that, in the arrangement illustrated in FIG. 7, the differentiator 44 performs the same function as the twin ratemeter arrangement described above.

The invention is not restricted to the details of the foregoing examples. For instance, instead of γ radiation X-rays or neutrons may be employed with appropriate adaptation of the source and detector system. The choice of radiation is, of course, influenced by the nature of the analysis to be carried out, the radiation giving the most appropriate back scattering effect for the material to be examined being selected from the extensive published data on nuclear interactions and their cross sections.

I claim:

1. A device for searching for low atomic number materials especially organic materials concealed by metal such as steel up to 12 millimeters thick, said device comprising a cylindrical end housing with a cylindrical side arm attached thereto, which side arm provides a convenient handle for holding the device, an annular scintillation crystal disposed close to a side wall of the housing, a short cylindrical collimator disposed within the central circular aperture of the said scintillation crystal, a capsule containing a radioactive material source of γ radiation mounted in said collimator at the end thereof remote from said side wall, the capsule having a tungsten alloy backing which shields against radiation emanating from the source in the direction away from the said side wall, a photomultiplier, a light guide providing an optical path for directing the light from scintillations in the scintillation crystal onto said photomultiplier, first and second ratemeter to both of which is fed the backscatter count provided by the output of the photomultiplier, said ratemeters having different rates of response to change in count rate, and a detector means for subtracting the output of one ratemeter from the output of the other ratemeter such that, under steady count rate conditions, the outputs of the ratemeters will become balanced and the detector means will provide a zero indication, and such that when the backscatter count rate changes, a difference between the ratemeter outputs which diminishes with time appears as a result of the different rates of response of the ratemeters to the change, an audible indicator device being connected to said detector means such that said differences will cause a change in the pitch of an audible indicator tone produced by said audible indicator device.

2. A device for searching for low atomic number materials especially organic materials concealed by metal such as steel up to 12 millimeters thick, said device comprising a cylindrical end housing with a cylindrical side arm attached thereto, which side arm provides a convenient handle for holding the device, an annular scintillation crystal disposed close to a side wall of the housing, a short cylindrical collimator disposed within the central circular aperture of said scintillation crystal, a capsule containing a radioactive material source of $\gamma$ radiation mounted in said collimator at the end remote thereof from the said side wall, the capsule having a tungsten alloy backing which shields against radiation emanating from the source in the direction away from the said side wall, a photomultiplier, a light guide providing an optical path for directing the light from scintillations in the scintillation crystal onto said photomultiplier, an amplifier, pulse shaper and ratemeter, the signal output from the photomultiplier being amplified by said amplifier and fed to said pulse shaper and thence to said ratemeter, the output of the ratemeter being a signal level indicative of a rate of receipt of pulses from the pulse shape and the signal level output from the ratemeter only changing when the pulse rate changes, a differentiator for indicating such changes in pulse rate, the differentiator providing a negative-going spike whenever the ratemeter level increases, means for cutting off a positive going spike form the differentiator in the event of a fall in ratemeter level, thereby to reduce the recovery time of the differentiator, an adjustable discriminator for testing negative going spikes against a trip level, and an indicator which is triggered whenever the change in the pulse rate exceeds a predetermined amount and which is adjustable by changing the setting of the trip level of the adjustable discriminator.

* * * * *